(12) United States Patent
Talieh

(10) Patent No.: US 7,871,375 B2
(45) Date of Patent: Jan. 18, 2011

(54) LED LIGHTING APPARATUS AND METHOD OF USING SAME FOR ILLUMINATION OF A BODY CAVITY

(75) Inventor: Yahya John Talieh, Modesto, CA (US)

(73) Assignee: Medical Vision Industries, Inc., Modesto, CA (US)

( * ) Notice: Subject to any disclaimer, the term of this patent is extended or adjusted under 35 U.S.C. 154(b) by 263 days.

(21) Appl. No.: 11/278,803

(22) Filed: Apr. 5, 2006

(65) Prior Publication Data

US 2006/0242884 A1 Nov. 2, 2006

Related U.S. Application Data

(60) Provisional application No. 60/668,907, filed on Apr. 5, 2005, provisional application No. 60/691,720, filed on Jun. 16, 2005.

(51) Int. Cl.
*A61B 1/32* (2006.01)
(52) U.S. Cl. .................. 600/249; 600/245; 600/199; 362/804
(58) Field of Classification Search ............... 600/249, 600/179, 199, 241, 245; 362/804; 433/29
See application file for complete search history.

(56) References Cited

U.S. PATENT DOCUMENTS

| | | | |
|---|---|---|---|
| 4,361,379 A | 11/1982 | Klein | |
| 5,302,124 A * | 4/1994 | Lansing et al. | 433/116 |
| 5,441,043 A | 8/1995 | Wood et al. | |
| 5,634,711 A * | 6/1997 | Kennedy et al. | 362/119 |
| 6,102,696 A * | 8/2000 | Osterwalder et al. | 433/29 |
| 6,159,005 A * | 12/2000 | Herold et al. | 433/29 |
| 6,193,510 B1 * | 2/2001 | Tsimerman | 433/29 |
| 6,211,626 B1 | 4/2001 | Lys et al. | |
| 6,217,512 B1 * | 4/2001 | Salo et al. | 600/160 |
| 6,283,612 B1 * | 9/2001 | Hunter | 362/240 |
| 6,406,293 B1 * | 6/2002 | Burstein | 433/29 |
| 6,528,954 B1 | 3/2003 | Lys et al. | |
| 6,591,049 B2 | 7/2003 | Williams et al. | |
| 6,595,917 B2 | 7/2003 | Nieto | |
| 6,692,251 B1 * | 2/2004 | Logan et al. | 433/29 |
| 7,195,482 B2 * | 3/2007 | Scott | 433/29 |
| 7,306,559 B2 * | 12/2007 | Williams | 600/245 |
| 7,311,722 B2 * | 12/2007 | Larsen | 607/88 |
| 2003/0076281 A1 * | 4/2003 | Morgan et al. | 345/44 |
| 2003/0218880 A1 * | 11/2003 | Brukilacchio | 362/293 |
| 2004/0141175 A1 * | 7/2004 | Baldwin et al. | 356/237.2 |
| 2005/0171407 A1 * | 8/2005 | Rosenkranz et al. | 600/249 |

* cited by examiner

*Primary Examiner*—Ralph A Lewis
(74) *Attorney, Agent, or Firm*—Pillsbury Winthrop Shaw Pittman LLP

(57) ABSTRACT

The present invention provides an LED lighting apparatus and a method of using the same for illumination of a body cavity. In one aspect, the present invention provides a method of surgery in which one incision is made for hands and surgical instruments, and another incision is made for insertion of an LED lighting device. Both incisions open into the same cavity, and the lighting device provides continuous internal lighting to the body cavity where the operation is occurring. In another aspect, a method and apparatus are described that provide internal chandelier lighting to an internal body cavity using a plurality of switched LED's for surgical without damaging tissue within the body cavity.

15 Claims, 7 Drawing Sheets

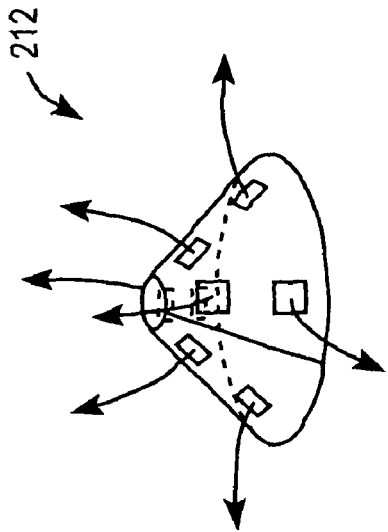
FIG. 2B2
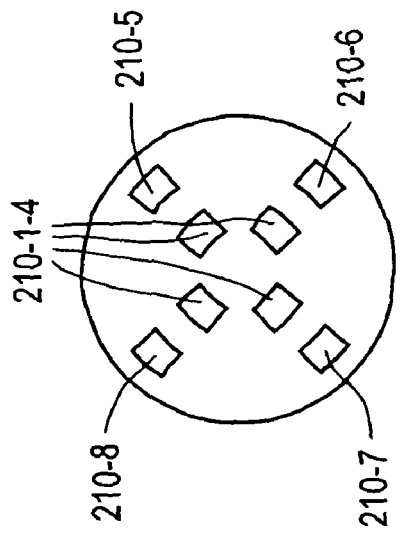
FIG. 2C
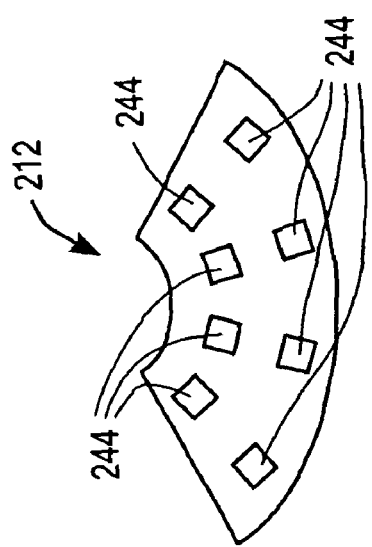
FIG. 2B1

US 7,871,375 B2

LED LIGHTING APPARATUS AND METHOD OF USING SAME FOR ILLUMINATION OF A BODY CAVITY

CLAIM OF PRIORITY

This application claims the benefit of priority to U.S. Provisional Application Ser. No. 60/668,907 filed Apr. 5, 2005 and to U.S. Provisional Application Ser. No. 60/691,720 filed Jun. 16, 2005, the entirety of which are incorporated herein by reference.

BACKGROUND OF THE INVENTION

1. Field of the Invention

The present invention relates to an LED lighting apparatus and a method of using the same for illumination of a body cavity, particularly a body cavity that has been exposed during a surgical procedure requiring an incision.

2. Background of the Invention

That various medical procedures require light is well known. For instance, it is well known that hospitals spend exorbitant amounts of money to provide surgeons with overhead lighting in surgery. Nonetheless, in large part to the obstruction in the path of light caused by the physical presence of the surgeon, overhead lighting alone may not, in many circumstances, be adequate.

External lighting such as light beams worn as a headset is also well known. While these have the advantage of not being obstructed by the physical presence of the surgeon, they introduce other issues, as they can be uncomfortable to wear, and also must have sufficient strength to travel distances of over 2 to 3 feet, from the top of the surgeon's head to the point of interest. Additionally, such headsets require the surgeon to position their head to direct the light in the appropriate direction, which can be cumbersome.

As a result, during surgical medical procedures that require incisions in order to gain access to a body cavity, incisions must be made sufficiently large in order to allow for the insertion not only of the instruments and the hands of the surgeon, but also for paths of light into the body cavity of interest, which can be detrimental to the patient.

It is also recognized that there exist lighting devices which can be temporarily inserted into a body and temporarily provide directed light to a particular internal body cavity area. Such insertion, however, requires a pair of hands to direct the light, and known devices do not provide sufficient illumination, both in terms of the area of illumination, as well as amount of light output.

SUMMARY OF THE INVENTION

The present invention provides LED lighting apparatus and a method of using the same for illumination of a body cavity.

In one aspect, the present invention provides a method of surgery in which one incision is made for hands and surgical instruments, and another incision is made for insertion of an LED lighting device. Both incisions open into the same cavity, and the lighting device provides continuous internal lighting to the body cavity where the operation is occurring. In another aspect, a method and apparatus are described that provide internal chandelier lighting to an internal body cavity using a plurality of switched LED's for surgical without damaging tissue within the body cavity.

In still another aspect, the present invention provides a method of using an internal lighting device that requires inserting a retractor that includes a plurality of LED's thereon underneath a body tissue, and then elevating or depressing the tissue using the retractor. With the tissue elevated or depressed, it is possible to view the area surrounding the elevated tissue using the light from the plurality of LED's.

BRIEF DESCRIPTION OF THE DRAWINGS

The above and other aspects of the present invention will become readily apparent when reading the following detailed description taken in conjunction with the appended drawings in which:

FIGS. 2A, 2B1 and 2B2 illustrate electrical circuits used in the lighting device according to the present invention;

DETAILED DESCRIPTION OF THE PREFERRED EMBODIMENTS

Figure 1:
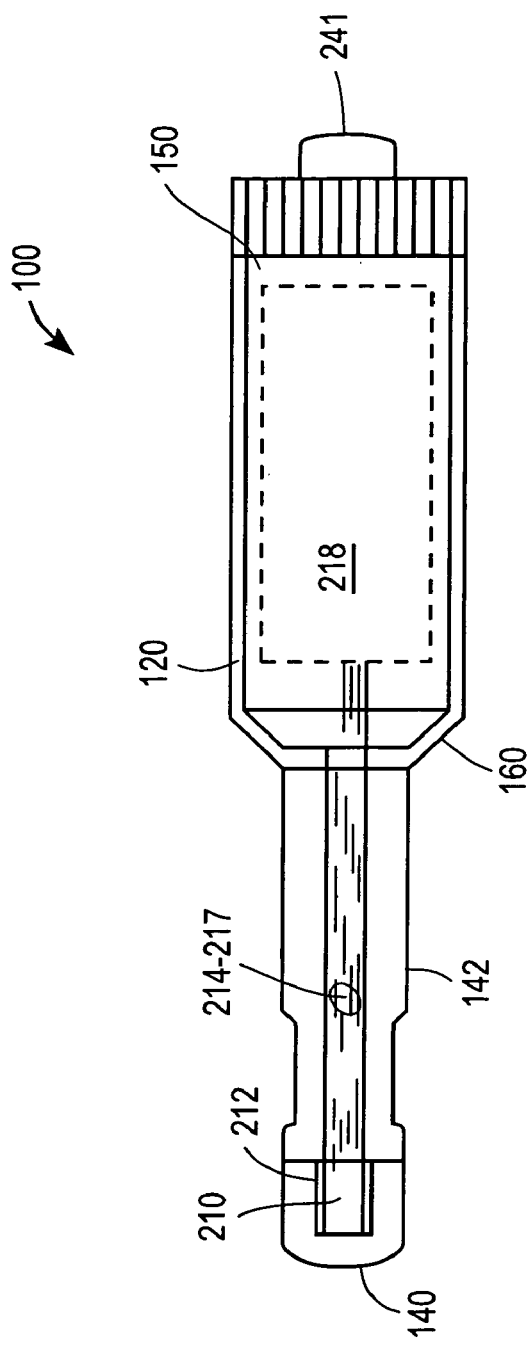
FIG. 1 illustrates a lighting device according to the present invention.

The present invention provides LED lighting apparatus and a method of using the same for illumination of a body cavity. While certain aspects of the invention are described in the context of a human body cavity, it will be understood that these aspects are equally applicable to body cavities of animals other than humans.

An embodiment of the LED lighting apparatus according to the present invention will first be described, and then a description of its use, both generally as well as particularly with reference to certain surgical procedures, is provided.

Handheld lighting device 100 contains an electrical lighting circuit 200, preferably fully contained within a housing 120. Light is transmitted radially outward in forward and side direction from an LED array 210 disposed within and at a transparent front tip 140 of the housing 120. The LED array 210 is connected through wires to electrical components that form the remainder of the electrical lighting circuit 200 and are formed within the rear 150 of the housing 120, as described hereinafter.

The transparent front tip 140 is preferably made of polycarbonate, and the housing 120 is preferably made of black Delrin plastic that is about 0.05" thick. The transparent front tip is preferably sealed onto the housing 120 using a sealant such as silicone rubber or a molding process. For most surgical uses, the device 100 is sterilized, transported in a sterile container, and intended for use only once, being disposed of thereafter.

The front tip 140 is narrower in cross-sectional area than the rear end 150, which allows for insertion of the front tip 140 into different body cavities, even those with smaller opening. The length of a front tip neck 142 is shown as approximately 1-3" long, with a diameter of about 0.5", roughly corresponding to a size 28 French chest tube. The rear end diameter is about 0.8", with the rear outer housing having a length of about 2". These dimensions are the dimensions for a preferred usage in a thoracic surgery environment, but will, depending on the application.

A mid-section transition area 160 has a slope that widens from the front tip neck 142 to the rear outer diameter. Area 160 facilitates in certain surgical procedures, such as thoracic surgical procedures described hereinafter, the device 100 to be self-supporting. The placement of the components in the rear end 150 helps weight the device 100 in a manner that assists in its ability to be self-supporting, as described hereinafter.

The electronic lighting circuit 200 is shown in FIG. 1 as having the LED array 210 mounted on a printed circuit board 212. Wires 214, 215, 216, and 217 connect the printed circuit board 212 to a printed circuit board 218 disposed within the rear 150 of the housing 120. Dimmer switch 241 provides a dimming function if desired, or can simply be an on-off switch.

Figure 2A:
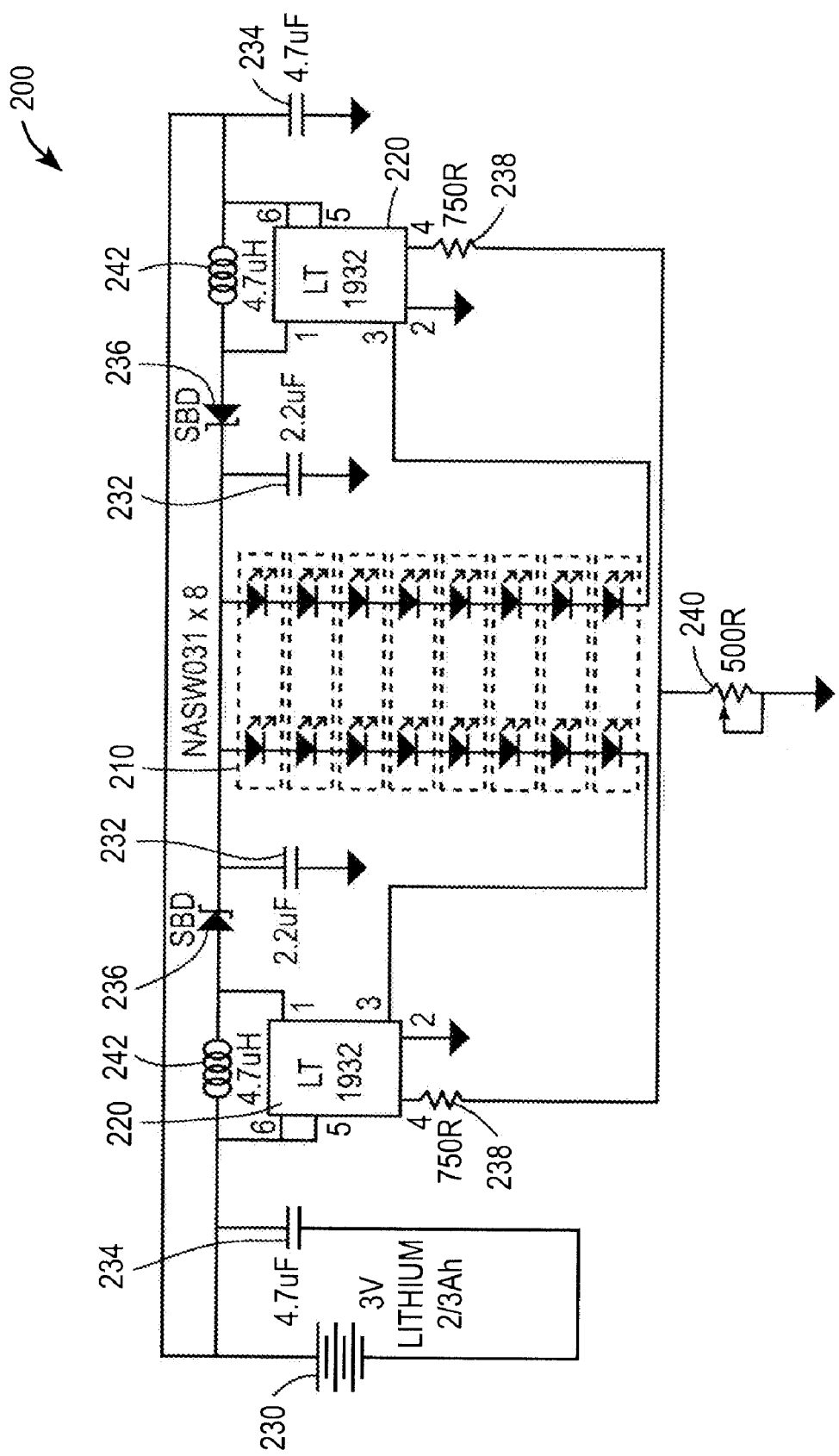

FIG. 2A illustrates the electronic lighting circuit 200 in further detail. As illustrated, the LED array 210 is preferably made of a plurality of white LED's. A preferred LED is a Nichia NASW031T. The array of 16 LED's 210-1 to 210-16 is illustrated as 2 sets of 8 LED's to illustrate that the each set of LED's 210-1 to 210-8 and LED's 210-9 to 210-16 are respectively switched using one of the two constant current source driver circuits 220. In this preferred embodiment shown, the two constant current source driver circuits 220 are Linear Technology LT1932 DC/DC Constant Current Source LED Driver Circuits, powered by a 3V Lithium battery 230. The remainder of the circuit components includes, as shown, capacitors 232 and 234, schottky barrier diodes 236, resistors 238 and 240, and inductors 242. As illustrated, resistor 240 provides a dimming function. Of course, many other different circuits can be used for switching the LED's and are intended to be within the scope of the invention.

FIG. 2B1 illustrates a preferred embodiment of the printed circuit board 212. As illustrated, printed circuit board 212 is thin and flexible, contains LED mounting areas 244 and connecting lines between them. Care needs to be taken that when folded into the cone shape as illustrated in FIG. 2B2, that the various LED's 210 can each maintain their surface mount. Each of the various LEDs 210 thus have a normal beam pointing in a different direction, and thereby achieving the chandelier lighting effect, with substantially uniform illumination in different directions over at least a radially increasing half sphere.

While the preferred embodiment described above used 16 different LED's 210, a lesser or greater number of such LED elements can be used. Significant to this embodiment, however, is that the normal beam of at least some of the LED's differs, particularly at least 3 LED's, provides for the most uniform chandelier illumination in all directions. It is noted, however, that for surgical operations performed on internal body cavities, that having an overall light output from the front tip 140 that is greater than 10 Candelas is adequate, and that an overall light output that is 20 Candelas or more is preferred.

In operation, the LED's 210 are each switched on and off using the constant current source driver circuit 210, and are preferably operated at less than their maximum operating point to assist in obtaining the whitest light for illumination, as well as keeping the heat generated by the LED's as low as possible, which is advantageous given that the front tip 140 will likely rest on internal body tissue in certain applications as discussed hereinafter.

It is noted that while the preferred embodiment uses a constant current source driver circuit, any number of different LED drivers can be used and still fall within the scope of the present invention. A constant current source driver circuit is preferred, however, as it provides for the most uniform illumination over hours of continuous illumination time.

FIG. 2C1 illustrates another embodiment of a printed circuit board 212A. As illustrated, in this instance the printed circuit board 212A is flat and round, and fits within the housing of the front tip 140. Four top view LED's 210-1 to 210-4 are each mounted on mounting areas 246, such that their normal beams are parallel and pointing up in the same upward direction, and four side view LED's 210-5 to 210-8 are each mounted on mounting areas 246 such that their normal beams are facing outward. With LED's 210 that are both side view and top view types, with a conical dispersion pattern of 110°, the chandelier lighting effect is also obtained.

Figure 3:
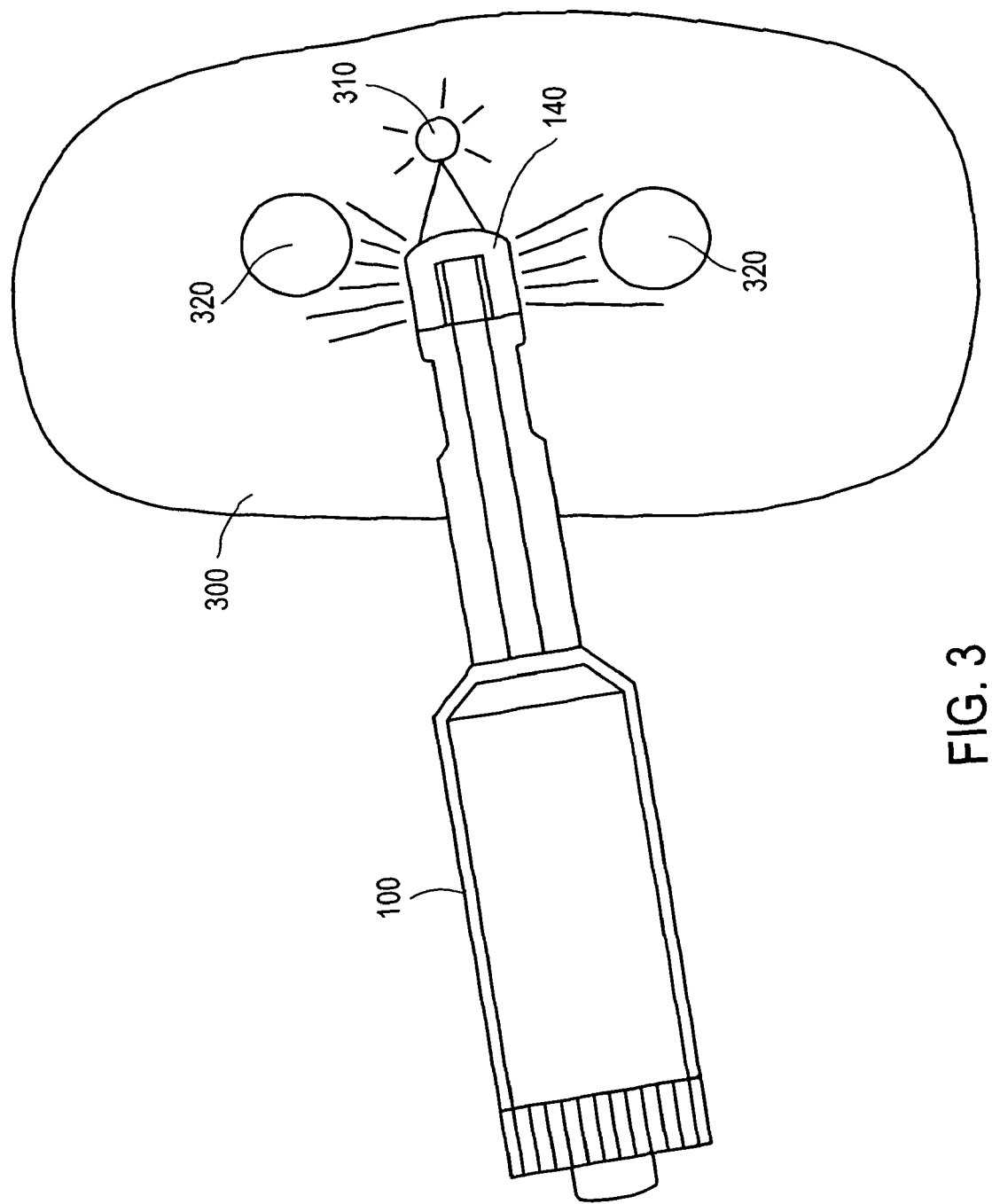
FIG. 3 illustrates a method of using the lighting device according to the present invention.

In use, as shown in FIG. 3, the lighting device 100 is inserted into a body cavity 300, which cavity can include a cavity opening for surgery, a mouth, a vagina, or other orifice. The chandelier illumination provided allows viewing of more areas that previously were difficult to see, particularly for larger cavities. As such, the lighting device 100 of the present invention allows for uniform illumination of areas over an internal range of over 12" from the front tip 140 in all directions around the front tip 140. This allows, as a result, illumination of an area 310 that is being focused upon using a lens of some type, as well as illumination of other areas 320 that are outside of the area 310 being focused on. With such illumination, without having to move his head or alter any lights, a surgeon can quickly and repetitively observe various different fields of vision.

Still furthermore, as a result of the very low heat generation due to the switched plurality of LED's 210, the lighting device 100 can remain inserted and the front tip 140 can remain pressed against internal body tissue (other than brain tissue) continuously for long periods, such as over 30 minutes and even hours.

Usage of the lighting device 100 for an inventive surgical method in a surgical procedure in which incisions are used in order to access an internal body cavity will now be described. Although the inventive surgical method will be described with reference to a specific thorocotomy procedure, a lung resection procedure, it will be understood that the inventive aspects described are applicable to other procedures in which incisions are used in order to access an internal body cavity.

The patient is initially placed in a lateral decubitus position using thorocotomy precautions including axillary roll, bean bag, and pillows between the legs. A band is used to elevate the arm at a right angle. The interior axillary hair line is clipped to expose the interior axilla (prior to prepping). The patient is prepped from the nipples to the spine using accepted sterile techniques.

Figure 4:
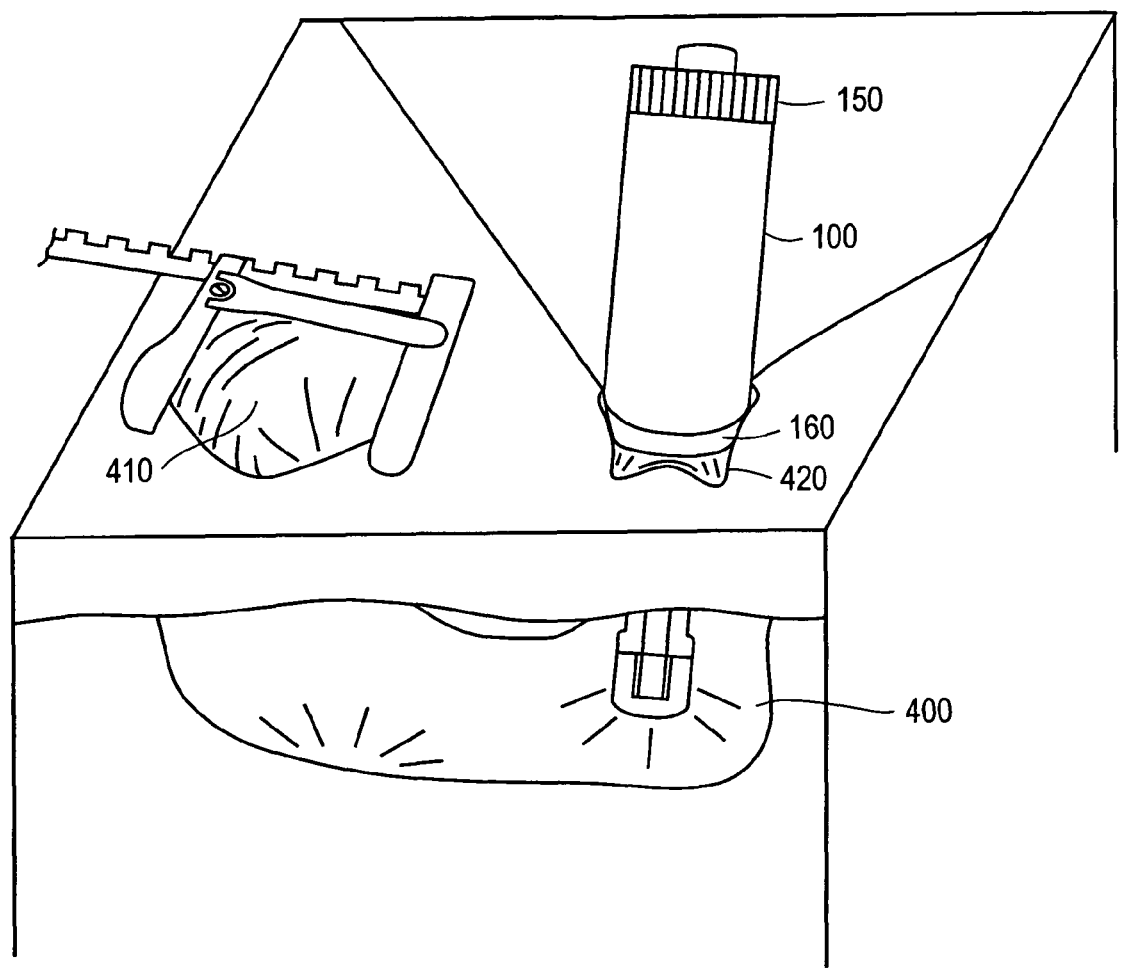
FIG. 4 illustrates a preferred method of using the lighting device according to the present invention for a surgical procedure requiring an incision to access an internal body cavity.

As shown in FIG. 4, a vertical incision 410 inferior to the axillary line is made going caudally, typically about 6-8 cm long, though with the present invention this can even be reduced to as small as 3-4 cm in certain circumstances. Take care to keep incision 410 at least 1 cm anterior to the border of the latissimus dorsi muscle. The incision 410 is carried through the subcutaneous tissue. The latissimus is retracted posteriority. The serratus is identified and divided along the course of its fibers, sparing the muscle. The insertion of the serratus muscles are taken down from the ribs to identify the proper intercostal space. The lung is deflated and the intercostal muscle is divided along the superior border of the rib extending anterior to the mammary vessels and posterior 1-2 cm above the symphatetic chain.

A rib retractor is placed to retract the ribs. A second retractor is placed perpendicular to the rib retractor to facilitate retraction of soft tissue.

A standard stab incision 420 is made anterior to the iliac spine (where standard chest tube placement occurs), which stab incision is about 2 cm long. A clamp is used to penetrate the pleural space. A finger can be used to dilate the hole. The lighting device 100 is placed through the stab incision 420 into the cavity. A simple skin stitch is used to secure the lighting device 100 in place, with the mid-section transition area 160 butting up against the skin of the patient, and assisting in keeping the lighting device 100 in position so that it does not move in a substantial manner, with the rear end 150 protruding from the body, thereby making it highly unlikely that the lighting device 100 would be inadvertently left inside the body cavity.

The lighting device 100 can then be adjusted to the desired illumination level, though as noted above, it is preferred that the amount of light exceeds 20 Candelas. With the lighting device 100 in place, the operation proceeds until essentially completed. During the procedure, the lighting device can remain continuously in place, and need not be touched by the surgeon, although there are instances in which manipulation of the light source may be desired When the procedure is essentially complete, the lighting device 100 is removed. A standard chest tube is placed under direct vision through the incision 410. Because the lighting device 100 had been in the incision 100 and preferably has a diameter that is the size of a standard chest tube, there already exists a dilated hole for insertion of the standard chest tube. Ribs are re-approximated using intercostal suture. The Serratus is oriented using interrupted vicryl sutures. The latissimus is returned to its normal position. The subcutaneous tissue is closed with vicryl. The incision 410 is then closed using the physician's preferred method.

With the method as described above and the lighting device 100 inserted into the chest cavity 400, illumination is thus provided from the inside, continuously through substantially the entire procedure. In particular, as illustrated, an incision 410 is used to gain entry into the chest cavity 400 and perform the operation, with the incision 410 being sufficiently large for hands and surgical instruments needed for the procedure. In addition to incision 410, incision 420 provides another path for entry into the chest cavity 400, and with the front tip 140 of the device 100 fully inserted, illumination is provided inside the chest cavity 400.

It is noted that usage of the device 100 in a surgical procedure on a body cavity that requires access through an incision allows for smaller and/or fewer incisions to be made. A primary reason for this is that incisions typically need to be made sufficiently large to ensure that not only can the hands and surgical instruments be properly positions, but additional extra space is needed to ensure that light can reach the inner portions of the cavity being operated upon. With the device 100 providing chandelier lighting internally, the extra space obtained from a larger incision is not needed.

Figure 5A:
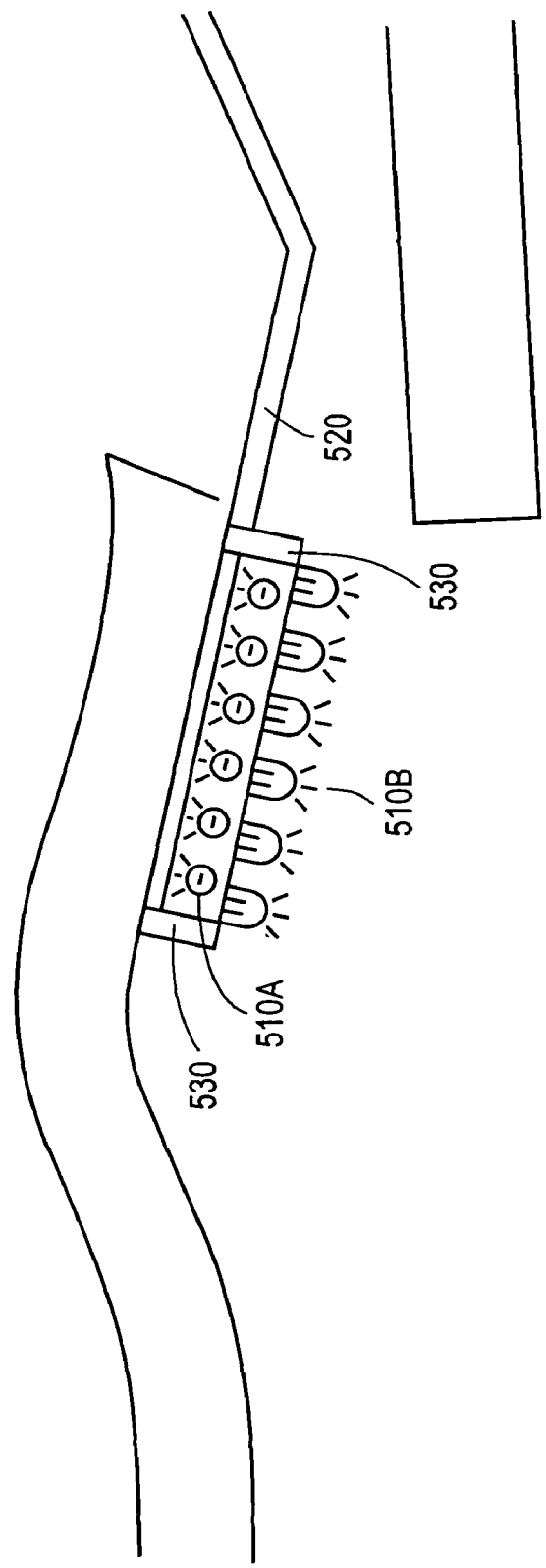
FIGS. 5A and 5B illustrate another embodiment of a lighting device according to the present invention.
Figure 5B:
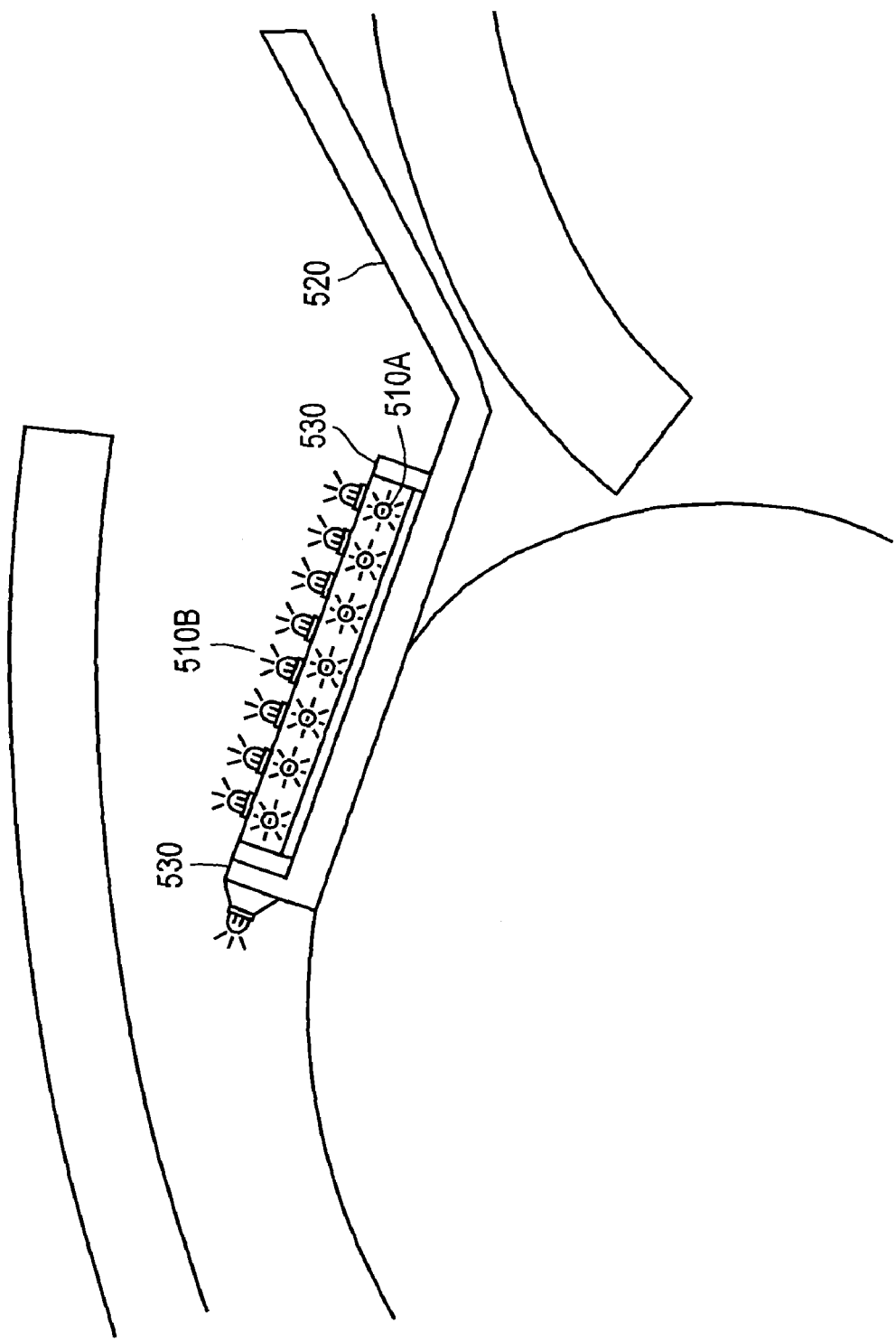

FIGS. 5A and 5B illustrates a lighting device 500 according to another embodiment of the present invention. As illustrated in FIG. 5A, LED's 510 are formed in an array, in this instance with their normal beams typically all being parallel or, as shown certain of the LED's 510A having normal beams parallel to each other, and other LED's 510B having normal beams that are parallel to each other and position at 90° with respect to LED's 510A. While it is also possible to include a third set of LED's 510C that are 180° opposite the LED's 510B, this third set of LED's 510C is not normally needed, and are not shown. In practice, the LED's 510 of this lighting device 500 are coupled to a retractor 520 using a coupling mechanism 530. The other portions of the circuit can be formed to also couple to the retractor 520

In use, this embodiment provides a method of using the internal lighting device 500 by inserting the retractor 520 that includes the plurality of LED's 510 thereon underneath a body tissue, and then elevating the tissue using the retractor 520 as shown in FIG. 5A, or depressing a tissue such as the lung shown in FIG. 5B. With the tissue elevated or depressed, it is possible to view the area surrounding the elevated tissue using the light from the plurality of LED's 520. Being able to depress the tissue and also view the depressed tissue has surgical advantages, as will be appreciated. In the FIG. 5B embodiment, the LED's 510 are arranged in include an LED 510 at the tip of the retractor 520, whereas such an LED 510 is not shown in the embodiment illustrated in FIG. 5A.

Modifications and variations of the preferred embodiment will be readily apparent to those skilled in the art. Such variations are within the scope of the present invention.

What is claimed is:

1. An apparatus that is for partial insertion through an incision in the outer skin surface on a torso of the body to an internal body cavity that has surrounding internal body tissue and provides internal chandelier lighting to the internal body cavity for use during a surgical procedure without damaging tissue within the body cavity, the apparatus comprising:

a sterile exterior housing having a tip end and a back end, wherein the tip end allows light to pass therethrough;

a plurality of switched LED's disposed within the sterile exterior housing at the tip end that are operated to enable placement of the tip end against internal body tissue for at least 30 minutes, the plurality of switched LED's including at least three LED's having normal beams that are different from one another and are operated at less than a maximum operating point to ensure a substantially white light and provide chandelier lighting, wherein the chandelier lighting provided by the plurality of switched LED's is at least 10 Candelas of substantially uniform illumination over at least a radially increasing half sphere around the tip end such that the substantially uniform illumination is sufficient for field of vision within the internal body cavity that is both magnified and non-magnified; and a power source that provided power to the plurality of switched LED's disposed within the sterile exterior housing, wherein the sterile exterior housing, the plurality of LED's and the power source form a unit, and wherein the unit is adapted to be self-supporting at an area of the exterior outer housing that widens between the tip end and the back end, and wherein the self-support is assisted by the unit being internally weighted to allow the exterior outer housing to balance at the area when the area rests upon the outer skin surface at the incision and the tip end is inserted through the incision.

2. The apparatus according to claim 1 wherein the plurality of switched LED's provide at least 20 Candelas of illumination.

3. The apparatus according to claim 2 wherein the plurality of switched LED's includes at least three LED's having normal beams that are different from one another to obtain substantially uniform illumination over at least a radially increasing half sphere.

4. The apparatus according to claim 1 wherein the plurality of switched LED operate using a constant current source to establish uniform illumination.

5. The apparatus according to claim 4 wherein the constant current source includes a stepper integrated circuit.

6. The apparatus according to claim 1 wherein the plurality of LEDs are each mounted on a printed circuit.

7. The apparatus according to claim 6 wherein the printed circuit board is cone shaped and mounted within the tip end so that a top of the cone shaped circuit board is disposed closer to the tip end then a base of the cone shaped circuit board.

8. The apparatus according to claim 7 wherein the plurality of LED's each have a normal beam pointing in a different direction.

9. The apparatus according to claim 6 wherein the printed circuit board is a flat circular shape.

10. The apparatus according to claim 6 wherein at least some of the plurality of switched LED's mounted to the cone shaped printed circuit board have normal beams that are different from one another to obtain substantially uniform illumination over at least a radially increasing half sphere.

11. The apparatus according to claim 1 wherein the plurality of LED's is at least 4, and different ones of the at least four LED's each illuminate a different illumination area.

12. The apparatus according to claim 1 wherein the sterile exterior housing, the plurality of LED's and the power source form a unit; and
further including a sterile container in which the unit is disposed prior to use.

13. The apparatus according to claim 1 wherein the power source is disposed in a back half of the exterior outer housing, closer to the back end then the tip end.

14. The apparatus according to claim 1 wherein the plurality of switched LED's includes at least one LED having a normal beam that is substantially parallel to a centerline of the sterile exterior housing and at least two LED's having other normal beams projecting toward a side of the sterile exterior housing.

15. The apparatus according to claim 14 wherein the plurality of switched LED's includes at least two LED's having the normal beam that is substantially parallel to the centerline of the sterile exterior housing and at least four LED's having the other normal beams projecting toward the side of the sterile exterior housing.

* * * * *